United States Patent [19]

Schilperoort et al.

[11] Patent Number: 4,684,611

[45] Date of Patent: Aug. 4, 1987

[54] PROCESS FOR THE IN-VITRO TRANSFORMATION OF PLANT PROTOPLASTS WITH PLASMID DNA

[75] Inventors: Robbert A. Schilperoort, Vincent van Goghlaan 40, 2343 RP Oegstgeest; Frans A. Krens, Scheveningen; George J. Wullems, Warmond, all of Netherlands

[73] Assignees: Rijksuniversiteit Leiden, Leiden; Robbert Schilperoort, Oegstgeest, both of Netherlands

[21] Appl. No.: 760,145

[22] Filed: Jul. 29, 1985

Related U.S. Application Data

[63] Continuation of Ser. No. 462,322, Jan. 31, 1983, abandoned.

[30] Foreign Application Priority Data

Feb. 11, 1982 [NL] Netherlands .......................... 8200523

[51] Int. Cl.⁴ ......................... C12N 15/00; C12N 5/00
[52] U.S. Cl. ............................ 435/172.3; 435/240.47; 935/56; 800/1
[58] Field of Search .................. 435/172.2, 172.3, 240; 47/1 R; 935/56

[56] References Cited

U.S. PATENT DOCUMENTS 4,394,448  7/1983  Szoka, Jr. et al. ................ 435/172.3

OTHER PUBLICATIONS

Lurquin, Archives Internationales de Physiologie et de Biochemie, vol. 87(4), pp. 824–825 (1979).
Lurquin, Plant Science Letters, vol. 21, pp. 31–40 (1981).
Davey et al., Plant Science Letters, vol. 18, pp. 307–313 (1980).
Kado, Recombinant DNA Technical Bulletin of the NiH, vol. 2, pp. 145–153 (1980).
Otten et al., Molec. Gen. Genet., vol. 183, pp. 209–213, (1981).
Fraley et al., Current Topics in Microbiology and Immunology, vol. 96, pp. 171–191 (1982).

*Primary Examiner*—Alvin E. Tanenholtz
*Attorney, Agent, or Firm*—Ladas & Parry

[57] ABSTRACT

Genetic properties of higher plants are transformed by incubating protoplasts of the plants together with plasmid DNA. The incubation is effected in the presence of polyethylene glycol and calcium ions. Subsequently—during after-incubation—the calcium ion concentration in the incubation medium is gradually increased and at the same time the polyethylene glycol concentration is decreased. The resulting aggregates are separated, grown further separately, and examined for modification of their genetic properties.

8 Claims, No Drawings

PROCESS FOR THE IN-VITRO TRANSFORMATION OF PLANT PROTOPLASTS WITH PLASMID DNA

This is a continuation of application Ser. No. 462,322, filed on 01/31/1983, now abandoned.

This invention relates to a process for the transformation of the genetic properties of higher plants by inserting the DNA of a foreign plasmid or part thereof into the DNA of these plants.

A controlled modification of the genetic system of living cells requires the possibility for DNA to be introduced into the host cells and to be taken up in the genome of the host in a reproducible manner. This has already been successfully applied to bacterial cells, yeast cells and mammalian cells, but not as yet to cells of higher plants, because in this case the cell wall formed too great a barrier. Attempts have been made, therefore, instead of plant cells to treat plant protoplasts in such a manner that foreign DNA is taken up in their genomes.

Thus plant protoplasts have just been incubated with bacterial plasmid DNA of *Escherichia coli* (Hughes, B. G., White, F. G., Smith, M. A., FEBS Lett. 1977, 79, 80-4; Owens, L. D., Plant Physiol. 1979, 63, 683-6). Moreover it has been tried to promote the uptake of this kind of DNA by adding to the incubation mixture polyethylene glycol or poly-L-ornithine or $Ca^{++}$ at pH10 (Lurquin, P.F. Arch., Int. Physiol. Biochim. 1979, 87, 824-5). Analogous experiments by means of poly-L-ornithine and the Ti plasmid DNA from *Agrobacterium tumefaciens* have been carried out by Davey et al. (Pl. Sci. Lett. 1980, 18, 307-313). Quite a different approach has been followed by first encapsulating the plasmid DNA from *E.coli* in liposomes, whereafter these are fused with plant protoplasts (Lurquin, P. F., Nucleic Acids Res. 1979, 6, 3773-3784).

In the studies by Hughes et al., Owens and Lurquin, it has been investigated by means of biochemical methods and techniques to what extent the foreign DNA is decomposed under the conditions applied, and whether there is any uptake by plant protoplasts. Lurquin concluded that polyethylen glycol and poly-L-ornithine, unlike $Ca^{++}$ at pH10 and lipsomes, do not give good results for the uptake of intact DNA by plant protoplasts. With the biochemical procedures applied in all these cases, however, it is not possible to show whether the treatment of the plant protoplasts adopted does actually lead to the foreign DNA penetrating the protoplasts, to a greater or lesser extent, and ultimately finding its way into the nucleus. It can only be concluded that after incubation foreign DNA is linked to the protoplasts. It is then still unkown whether this DNA is just present at the surface, or whether it has also penetrated the protoplasts. Even in those cases (see Hughes) in which the foreign DNA is found in nuclei isolated from protoplasts treated with DNA, it is questionable whether the DNA has arrived there through uptake by the plant protoplasts. In fact, it cannot be excluded that during the isolation of the nuclei foreign DNA bound at the surface of the protoplasts was released and was subsequently re-bound to the nuclei.

Not until it has been shown that foreign DNA in plant cells expresses itself and/or has been integrated into the host genome can it be concluded with certainty that there has been transformation of plant protoplasts with foreign DNA. Davey was only looking for the occurrence of DNA transformation, and Owens has also investigated this. In no case whatsoever was a stable or definitive DNA transformation observed.

Polyethylene glycol is not only used in experiments purporting to transform cells with DNA, but is also used for fusing intact cells which may be of quite different origins. Thus Yamada and Sakaguchi (Agric. Biol. Chem., 1981, 45, 2301-2309) caused certain bacteria to be taken up by yeast protoplasts (*Saccharomyces cerevisiae*). Wullems et al. (Theor. Appl. Genet., 1980, 56, 203-208) obtained, by means of polyethylene glycol, somatic hybrids by the fusion of plant protoplasts from normal cells and crown gall cells. The crown gall cells were obtained from tumors on tobacco caused by the bacterium *Agrobacterium tumefaciens*. The tumor cells contain a piece of bacterial DNA which is also maintained in the somatic hybrids. Accordingly, in the case of the crown gall cells, foreign, bacterial DNA has been incorporated in a natural manner by a bacterium without the use of in-vitro DNA transformation.

The natural transformation of the DNA in cells of higher plants by *A. tumefaciens*, which causes the crown gall disease, has long since been known, and occurs in various dicotyledonous plants. Monocotyledonous plants, including wheat, barley and other grains, however, are insensitive to this bacterium.

This bacterium—without itself penetrating the cell—inserts a portion of a tumor-inducing plasmid (TI plasmid) into the plant DNA of the dicotyledons, whereby a tumor-specific enzyme is formed in the transformed cells, which provides for the formation of the amino acid derivatives octopine or nopaline, which substances are a good source of carbon and nitrogen for the infecting bacterium. The DNA from the bacterial plasmid thus inserted is referred to as T-DNA. Situated on this T-DNA are also genes providing for an auxinic and cytokininic activity in the tumor cells, permitting unlimited growth of the same into a tumor, and permitting them to display hormone-autotrophic growth in the tissue culture.

It has now been found that corresponding transformations of the DNA of higher plants—both monocotyledons and dicotyledons—can be effected without the intermediary of infecting bacteria by incubating protoplasts of higher plants together with plasmid DNA in the presence of polyethylene glycol and calcium ions, and preferably in the presence of DNA molecules, in particular calf thymus DNA as a carrier, subsequently gradually increasing both the calcium ion concentration in the incubation medium and decreasing the polyethylene glycol concentration, separating the resulting colonies or cell clumps from each other, propagating them separately, and investigating them as to a modification of their genetic properties.

The following tests were conducted using protoplasts from leaves of aseptically cultivated *Nicotiana tabacum* SR1 shoots. After an enzymatic removal of the cell walls, these protoplasts were cultured in a K3 medium supplemented with phytohormones, which medium had the following composition:

1.1 mmoles/l $NaH_2PO_4 \cdot H_2O$; 0.4 mmole/l $CaHPO_4 \cdot 2H_2O$; 6.0 mmoles/l $CaCl_2 \cdot 2H_2O$; 25 mml/l $KNO_3$; 3.0 mmoles/l $NH_4NO_3$; 1.0 mmole/l $(NH_4)_2SO_4$; 1.0 mmole/l $MgSO_4 \cdot 7H_2O$; 4.5 µmoles/l KJ; 50 µmoles/l $H_3BO_3$; 60 µmoles/l $MnSO_4 \cdot H_2O$; 7.0 µmoles/l $ZnSO_4 \cdot 7H_2O$; 1.0 µmole/l $Na_2MoO_4 \cdot 2H_2O$; 0.1 µmole/l $CuSO_4 \cdot 5H_2O$; 0.1 µmole/l $CoCl_2 \cdot 6 H_2O$; 100 µmoles/l $Na_2 \cdot EDTA$; 100 µmoles/l $FeSo_4 \cdot 7$-

H$_2$O; 100 mg/l inositol; 1.0 mg/l nicotinic acid; 1.0 mg/l pyridoxine. HCl 10.0 mg/l thiamine.HCl, and 0.4 mole/l sucrose, dissolved in distilled water and having a pH=5.6.

The occurrence of transformed protoplasts appears from growth on phytohormone-free mediums, the formation of lysopine-dehydrogenase (LpDH) and the presence of T-DNA in the plant DNA. The transforming plasmid used for this purpose was the Ti plasmid DNA of *A. tumefaciens*. This Ti plasmid DNA was dissolved in a suitable concentration in sterile water, and with chloroform to prevent infection, stored for use at 4° C.

In the test proper, the protoplasts and the Ti plasmid DNA were incubated jointly in a polyethylene glycol containing solution in the presence of 50 µg calf thymus DNA as a carrier, followed by a subsequent incubation in the presence of calcium ions. The highest percent of transformation in the *N.tabacum* DNA was found to be reached with polyethylene glycol concentrations of between 7 and 20% (mg/cm$^3$), in particular of 12–15%, and a calcium ion concentration of approximately 40 mmoles/l in the first incubation, a gradual increase of the calcium ion concentration during the after-incubation to 100–125 mmoles/l with a simultaneous decrease in polyethylene glycol concentration to approximately between 1 and 3%, in particular between 1.6 and 2%. It has been found that particularly good results are obtained if during the incubation the weight ratio of the T-DNA to the calf thymus DNA is 1:5, while the after-incubation mixture is added incrementally.

When the process was carried out in the manner described above, various tissue lines were produced with clearly modified properties based on an insertion into the *N-tabacum* DNA of different pieces of the Ti plasmid DNA.

Thus tissue lines were found that grow without the addition of phytohormones, but exhibit no LpDH activity. From these tissue lines, plant regenerates (shoot formation) could be obtained in an early stage after the DNA transformation. Other lines also grew without the addition of phytohormones, but did exhibit an LpDH activity. A further line exhibited LpDH activity but failed to grow without the addition of phytohormones.

Obtaining shoots in an early stage is of essential importance for plant breeding purposes, because it is known that when regeneration does not occur until after a prolonged tissue culturing period (involving re-inocculation many times) there is a great chance that undesirable changes in the chromosome compositions occur. Moreover, the capacity to regenerate is often lost for plant tissue that has been maintained in the culture for a long time.

Further evidence that Ti plasmid DNA had been incorporated into the *N. tabacum* DNA in the tissue lines with modified properties was obtained by isolating the DNA of the modified tissue lines produced, cleaving it with restriction-endonuclease SmaI, and fractionating the fragments thus formed by electrophoresis over agarose gel. This procedure revealed for two lines which exhibited both LpDH activity and growth without the addition of phytohormones, as T-DNA successive restriction-enzyme fragments 17, 16a and 10c characteristic of the Ti plasmid used. A number of tissue lines exhibiting regeneration were also found to contain T-DNA. This T-DNA, however, did not consist of the complete restriction fragments referred to.

The process according to the invention accordingly offers the possibility of making mutants of higher plants with genetically improved or modified properties. This, as stated before, is of great importance for the plant breeding industry, the more so as the tissue lines obtained using the process according to the invention permit obtaining the regenerates in an early stage after the DNA transformation.

Furthermore the cells with autotrophic growth obtained using the process according to the invention, for example, the Crown gall cells, for a proper growth in a fermentator only require a very simple synthetic medium to which, for one thing, no phytohormones need be added. Cells thus produced, into which foreign DNA has been introduced, can be cultured on a large scale for the production of substances coded for by the foreign DNA, such as alkaloids, amino acids, hydrocarbons, proteins, enzymes, steroids, etc. (cf. Impact of Applied Genetics, Micro Organisms, Plants and Animals, OTA Report, Congress of the United States Office of Technology Assessment, Washington, 1981).

The invention is illustrated in and by the following example.

EXAMPLE

*Nicotiana tabacum* SR$_1$ protoplasts were isolated from leaves of sterile shoots and suspended, in a density of 5.10$^5$ protoplasts/cm$^3$, in a K$_3$ medium as described hereinbefore, supplemented with 0.1 mg naphthalene acetic acid per litre and 0.2 mg kinetine per litre. Cf. L.Marton et al., Nature 277, 129–131 (1979)).

From this suspension, fractions of 1 cm$^3$ were taken, to which 0.5 cm$^3$ of a fusion medium was added (cf. Theor. Appl. Genet. 56, 203 (1980)), in which a concentration of 40% (mg/ml) polyethylene glycol having an average molecular weight of 6000 had been dissolved, and which contained 140 mmoles/l NaCl, 5 mmoles/l KCl, 0.75 mmole/l Na$_2$HPO$_4$, 5 mmoles/l glucose and 125 mmoles/l CaCl$_2$.2H$_2$O, and the pH of which was 7.0. Subsequently 10 µg pTi Ach 5 DNA (from a solution containing 0.4 mg/cm$^3$) and 50 µg calf thymus DNA (from a solution containing 1 mg/cm$^3$) were added. Upon this, the protoplasts clustered together to form aggregates. These protoplasts were incubated, with occasional shaking, at 26° C. for 30 minutes. Thereafter 10 cm$^3$ of the above fusion medium—that is to say, without polyethylene glycol being added thereto—were added in portions of 2 cm$^3$ with intervals of 5 minutes. During the after-incubation, the aggregates were broken up again, collected by means of centrifugation, while the liquid was removed. The protoplasts were resuspended in 10 cm$^3$ K$_3$ medium with the concentrations of sucrose and hormones as specified before, and after the addition of 250 µg/cm$^3$ carbenicillin plated in petri dishes of 10 cm.

After being kept in the dark for 24 hrs. and subsequently exposed with 2000 lux for 12 hrs. a day, more than 50% of the cells were found to have survived the treatment. A fortnight later, 5 cm$^3$ K$_3$ medium with the concentrations of sucrose and hormones specified before were added. When the colonies were large enough, they were placed in a solid agar/K$_3$ medium which now, however, contained 0.3 mole/l sucrose, still supplemented with phytohormones. After being grown on this medium for about 1 month, the small calli formed were plated on a hormone-free K$_3$ medium, which now however contained 0.2 mole/l sucrose and 0.5% agar. Calli which continued to grow in this medium after one or two passages were plated in a hormone-free LS medium (cf. Nature 277, 129–131 (1979)).

This LS medium has the following composition:
18.8 mmoles/l $KNO_3$; 20.6 mmoles/l $NH_4NO_3$; 3.0 mmoles/l $CaCl_2.2H_2O$; 1.5 mmoles/l $MgSO_4.7H_2O$; 1.25 mmoles/l $KH_2PO_4$; 5 μmoles/l KJ; 100 μmoles/l $H_3BO_3$; 100 μmoles/l $MnSO_4.4H_2O$; 30 μmoles/l $ZnSO_4.4H_2O$; 1 μmole/l $Na_2MoO_4.2H_2O$; 0.1 μmole/l $CuSO_4.5H_2O$; 0.1 μmole/l $CoCl_2.6H_2O$; 100 μmoles/l $Na_2EDTA$; 100 μmoles/l $FeSo_4.7H_2O$; 87.6 mmoles/l (30 g/l) sucrose; 100 mg/l inositol and 0.4 mg/l thiamine, dissolved in distilled water and of pH=5.6.

On this the transformed lines were observed and subsequently examined for LpDH activity. Twelve callus lines were found to grow further on a phytohormone-free medium after the transformation, the percentage of the isolated transformants relative to the number of protoplasts used being $10^{--}10^{-4}$. Six of these lines exhibited a clear LpDH activity. Both transformation properties can only have been derived from inserted pieces of Ti plasmid. Moreover, this so-called T-DNA was demonstrated for all tissues.

We claim:

1. A process for transforming genetic properties of higher plants or parts thereof by inserting into the DNA of these plants DNA of a plasmid that is foreign to these plants, characterized by initially incubating protoplasts of higher plants together with plasmid DNA in the presence of polyethylene glycol, calcium ions, and carrier DNA, subsequently, after a period of incubation, gradually increasing the calcium ion concentration in the incubation medium, and decreasing the polyethylene glycol concentration wherein said calcium ion concentration is increased to 100–125 mmoles/l with a simultaneous decrease in said polyethylenCe glycol concentration to about 1–3% (weight/volume) separating the resulting aggregates, growing these further separately, and examining them for modification of their genetic properties.

2. A process according to claim 1, characterized by selecting a polyethylene glycol concentration of 12–15% (weight/volume) and a calcium ion concentration of about 40 mmoles/l during the initial incubation.

3. A process according to claim 1, characterized in that after a period of incubation the calcium ion concentration is increased incrementally to 125 mmoles/l with a simultaneous incremental decrease in the polyethylene glycol concentration to 1.8% (weight/volume).

4. A process according to claim 1, characterized in that the incubation is carried out in the presence of calf thymus DNA as a carrier.

5. A process according to claim 4, characterized in that during the incubation the weight ratio of foreign plasmid DNA to calf thymus DNA is 1:5.

6. A process for the preparation of chemical and/or pharmaceutical products, characterized by culturing cells produced by the process as claimed in claim 1, and isolating the desired substance.

7. A process according to claim 6, characterized in that culturing is effected by means of fermentation and subsequent mobilization.

8. A process, as in claim 1, characterized in that after a period of incubation said polyethylene glycol concentration is incrementally decreased to 1.6–2% weight/volume.

* * * * *